United States Patent [19]

Hofmann

[11] Patent Number: Plant 7,087

[45] Date of Patent: Dec. 26, 1989

[54] DISTINCT VARIETY OF GERANIUM PLANT NAMED LAURA

[75] Inventor: Christa Hofmann, Dresden, German Democratic Rep.

[73] Assignee: Oglevee Ltd., Connellsville, Pa.

[21] Appl. No.: 298,511

[22] Filed: Jan. 18, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new cultivar Laura is characterized by its color and growing performance. The bright lavender-pink bloom draws the attention with the addition of a white eye as accent. The overall plant habit is compact but well branching with an attractive green foliage. The plant holds up well outdoors withstanding most weather conditions.

1 Drawing Sheet

BACKGROUND OF THE NEW PLANT

The present invention comprises a new and distinct cultivar of *Pelargonium hortorum* which is a zonal florists geranium known by the varietal name of Laura. The new variety was discovered in a selective breeding program by Mrs Christa Hofmann and is a selection from the crossing of the varieties Rospen, Yvonne, Dresden and Dressdner Puppe.

The new cultivar was discovered in the year 1983 in the VEB Saatzucht Zierpflanzen, Dresden, German Democratic Republic; was first asexually reproduced by cuttings in Dresden, German Democratic Republic, and has been repeatedly asexually reproduced for over two years by cuttings for Oglevee Associates, Inc. in Connellsville, Pa. It has also been trialed and field tested and has been found to retain its distinctive characteristics through sucessive propagations.

The new cultivar, when grown in a greenhouse in Connellsville, Pa., using natural light, 60° F. night temperature, 68° F. day temperature, and 71° F. vent temperature, has a response time of eight weeks from a well-rooted cutting to a flowering plant in a four inch (10 cm) pot.

DESCRIPTION OF THE DRAWING

The accompanying photographic drawing illustrates a new cultivar, the color being as nearly true as possible with color illustrations of this type.

DESCRIPTION OF THE NEW PLANT

The following detailed description set forth the characteristics of the new cultivar. The data which defines these characteristics were collected from asexual reproductions carried out for Oglevee Associates, Inc. in Connellsville, Pa. The plant history was taken on eight-week plants, blossomed under natural light in a greenhouse, and color readings were taken indoors under 200–220 foot candles of cool white fluorescent light. The rooted cuttings of the test plants were potted on Aug. 4, 1987 and flowered on Sept. 20, 1987. The plants were grown in a soilless media with constant fertilizer of 250–275 parts per million nitrogen and potassium and full light. Color references are primarily to the R.H.S. Colour Chart of The Royal Horticultural Society of London.

THE PLANT

Classification:

*Botanical.*—*Pelargonium* × *hortorum* bailey.

*Commercial.*—Zonal geranium.

Form: Bush. Basal branching, free and early flowering, upright habit.

Height: 28.0–31.0 cm from media surface.

Growth: Free-branching from base; medium internode length.

Strength: Stands upright without artificial support.

Foliage: Medium-sized leaves with very little zonation.

Leaves: Leaf description of a mature, fully expanded leaf at least four nodes below apical meristem.

*Size.* 8.0–12.0 cm wide.

*Shape.*—Reniform, cordate base.

*Margin.*—Crenate.

*Texture.*—Pubescent, dull (not reflective).

*Color.*—Green group 137B.

*Ribs and veins.*—Palmate veination Green group 138B.

Petioles: Stalked petiole 7.0–10.0 cm, Green group 137C.

Stem:

*Color.*—Green group 143A.

*Internodes.*—The internode length between mature leaves is 2.5–4.0 cm.

THE BUD

Shape: The umbel contains 30–40 flower buds and is uniformly convex.

Size: The umbel varies in size from 8.0–15.0 cm.

INFLORESCENCE

Blooming habit: Continuous, upright, semi-double, hemispherical in shape.

Size: 8.0–15.0 cm.

Borne: Umbel; florets on pedical, pedicel on peduncle; 4.0–9.0 cm above foliage.

Tonality from distance: Lavender with a white center on medium green foliage.

Florets:

*Form.*—Flat to slightly cupped; with petaloids; obovate.

*Color.*—Red-purple group 67B; approximately 1.5 cm of each petal from basal end is white (front).

*Petals.*—5–8 separate-not united; margin entire; obovate; palmate veination; smooth flat to slightly cupped.

*Size.*—5.0 cm.

*Texture and appearance.*—Smooth.

Petaloids:

*Quantity.*—5–7.

*Shape.*—Narrow, elongated, twisted with some larger being obovate.

*Color.*—Top — Red-purple group 67B. Bottom — Red-purple group 68A.

Pedicel:

*Length.*—2.5–4.0 cm; apical — Red group 53A; basal end — Yellow-green group 144A.

Peduncle: Arises from node, opposite leaf petiole; 1.0–20.0 cm in length; Yellow-Green group 144A.

Lasting quality:

*Normal.*—Up to two weeks.

REPRODUCTIVE ORGANS

Stamens:

*Anthers.*—Elliptical; 1.0–1.5 mm.

*Filaments.*—White at base with gradual coloring to tip, irregular in shape; some petaloid, flat at base and twisted at tip, 5.0–7.0 mm in length.

*Pollen.*—Golden brown.

Pistils:

*Number.*—One with 5–6 parted stigma.

*Length.*—5.0 cm.

*Stigma.*—5–6 parted; color same as floret.

*Style.*—One, reddish color, 2.0–3.0 mm in length.

Ovaries: 6.0–7.0 mm in length, yellow-green, pubescent; superior.

Fruit: None observed.

The new cultivar Laura is an outstanding new plant, both in color and growing performance. The bright lavender-pink bloom draws the attention with the addition of a white eye as accent. The overall plant habit is compact but well branching with an attractive green foliage. The plant holds up well outdoors withstanding most weather conditions.

I claim:

1. A new and distinct variety of geranium plant characterized by a bright lavendar-pink bloom having a white eye as accent, a compact plant habit with good branching and an attractive green foliage, and long lasting quality under most weather conditions, substantially as herein shown and described.

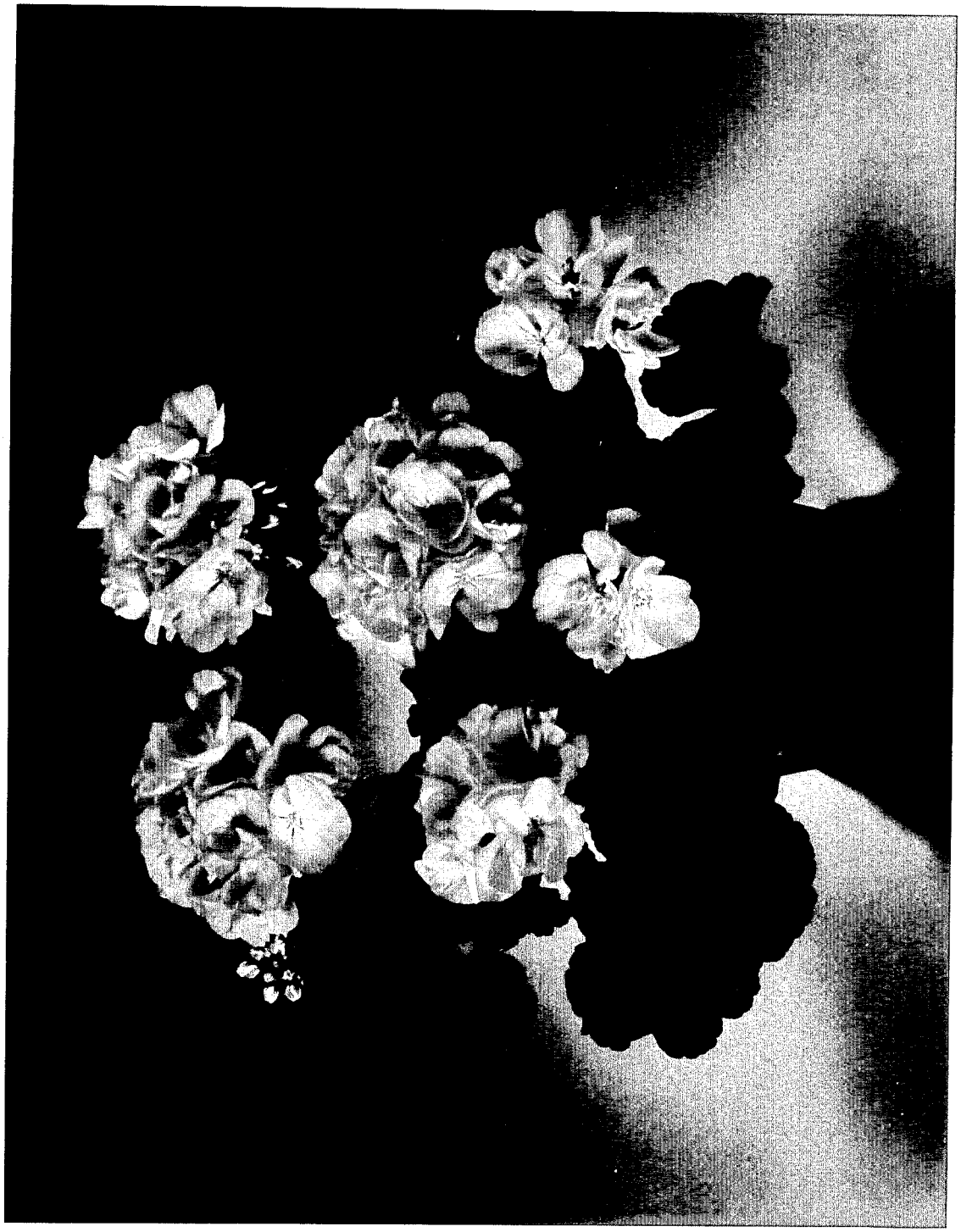

* * * * *